United States Patent [19]
Dürr et al.

[11] Patent Number: 5,547,324
[45] Date of Patent: Aug. 20, 1996

[54] MEMBER PROVIDED WITH AN EXTERNAL SCREW THREAD

[75] Inventors: Walter Dürr, Remchingen; Axel Kirsch, Filderstadt, both of Germany

[73] Assignees: Eberle Medizintechnische Elemente GmbH, Wurmberg; IMZ Fertigungs-und Vertriebsgesellschaft für dentale Technologie mbH, Filderstadt, both of Germany

[21] Appl. No.: 965,381

[22] PCT Filed: Apr. 7, 1992

[86] PCT No.: PCT/DE92/00292

§ 371 Date: Jan. 15, 1993

§ 102(e) Date: Jan. 15, 1993

[87] PCT Pub. No.: WO92/18780

PCT Pub. Date: Oct. 29, 1992

[30] Foreign Application Priority Data

Apr. 20, 1991 [DE] Germany .......................... 41 13 411.7

[51] Int. Cl.⁶ ................ F16B 39/34; A61C 8/00
[52] U.S. Cl. ............................. 411/304; 411/418
[58] Field of Search ................ 411/302, 303, 411/304, 411, 417, 418; 606/73; 433/174

[56] References Cited

U.S. PATENT DOCUMENTS

| | | |
|---|---|---|
| 2,568,640 | 9/1951 | Kindelberger . |
| 2,730,154 | 1/1956 | Aspey ................................ 411/418 |
| 2,852,056 | 9/1958 | Rapata . |
| 3,182,702 | 5/1965 | Nason et al. . |
| 3,195,599 | 7/1965 | Brook ................................ 411/304 |
| 3,319,689 | 5/1967 | McDougall et al. . |
| 3,439,575 | 4/1969 | Gifford . |
| 4,334,865 | 6/1982 | Borle ................................ 433/174 |
| 5,026,285 | 6/1991 | Dürr et al. . |
| 5,125,840 | 6/1992 | Dürr et al. . |

FOREIGN PATENT DOCUMENTS

| | | |
|---|---|---|
| 56625 | 7/1982 | European Pat. Off. ............ 297/327 |
| 975912 | 3/1951 | France ................................ 411/304 |
| 770696 | 3/1957 | United Kingdom . |

*Primary Examiner*—Flemming Saether
*Attorney, Agent, or Firm*—Hill, Steadman & Simpson

[57] ABSTRACT

The invention relates to a member provided with an external screw thread, in which at least in the end portion of the screw thread is provided with at least one plastic part for at least partially covering the same and/or at least partially replacing the same.

16 Claims, 2 Drawing Sheets

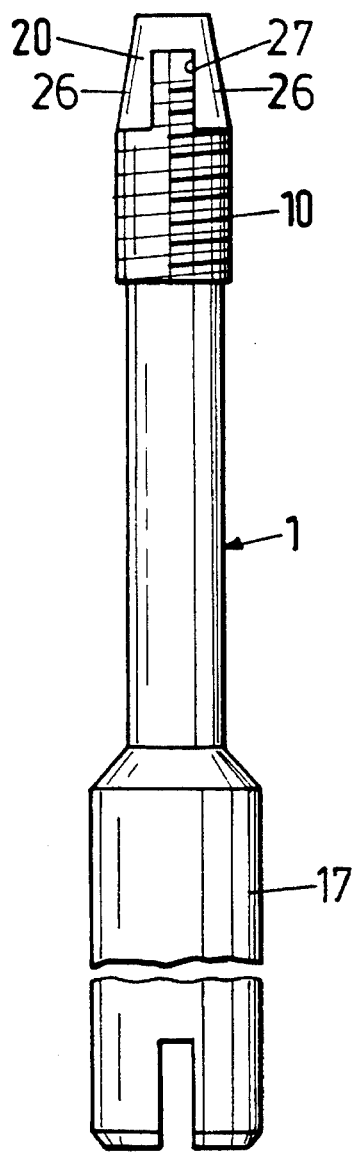
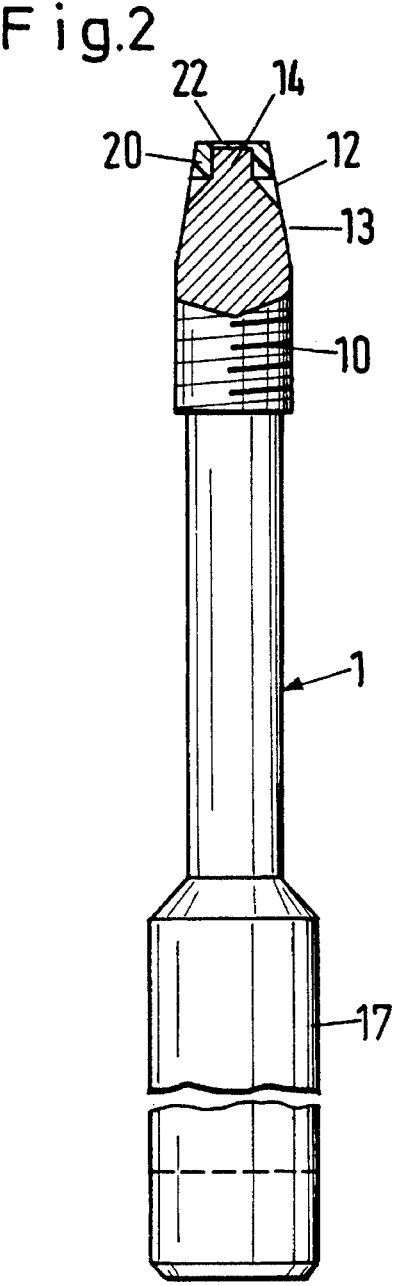
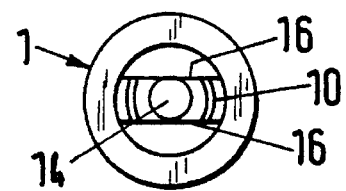

MEMBER PROVIDED WITH AN EXTERNAL SCREW THREAD

BACKGROUND OF THE INVENTION

The invention relates to a member provided with an external screw thread.

As a function of the intended use and in the case of screw connections, it is important to a greater or lesser extent to prevent loosening by means of a rotation preventing means. It is therefore inevitable e.g. in dental prosthetics, for screw connections to have a detachable, but firm seating. Loosening must in particular be prevented in the case of parts which are directly screwed into an implant, such as e.g. implant extensions, implant posts, attachment posts, etc., or in the case of screws used for fixing crowns, bridges and other structures in dental prosthetics.

German patent 39 17 690 already discloses for this purpose a spacer sleeve stop, which has a ring nut-like construction and which can be screwed by means of an internal lock thread with a much smaller pitch than the insert thread of a spacer sleeve bottom onto an external thread provided on the bottom close to the distal edge. Thus, the member, the spacer sleeve top and spacer sleeve bottom can be locked and braced together, which prevents rotation of both the spacer sleeve bottom which receives the implant post and the spacer sleeve top.

German patent application P 40 28 855.2 (addition to German patent 39 17 690) describes a corresponding further development of the rotation-prevented individual tooth implant according to the main patent, in which rotation is reliably prevented by simpler means using positive engagement chambers or members.

Both from the aforementioned prior art regarding single tooth implants and other members provided with external screw threads in the field of dental prosthetics and the like, no rotation prevention means is known which can do without some type of positive engagement. As a result the construction of such rotation prevention means in the given dimensions of the implant or prosthetics is often complicated or relatively expensive.

SUMMARY OF THE INVENTION

The object of the invention is to provide a member preventing in a particularly simple and inexpensive manner an extraction or loosening of the screw connection.

According to the invention this object is obtained in that at least an end portion of the screw thread is provided with at least one plastic part which has skirt means for at least partly covering the thread and/or at least partly replacing the thread.

Due to the fact that in portions of the screw thread there is a direct contact between the inventive plastic part and the corresponding internal screw thread, there is a squeezing of the plastic material in these portions during screwing in the screw. As a result of the frictional contact brought about in this way, a reliable rotation prevention is ensured in a surprisingly simple and effective manner.

The invention optionally provides for an attachment on the tip of the screw thread and in the extension thereof and which engages with a corresponding recess or socket in the plastic part. This ensures that the inventive plastic part can be placed in a simple and reliable manner on the screw thread tip.

It is particularly preferred if both the attachment and the recess in the plastic part are cylindrical and are positioned centrally with respect to the cross-section of the screw thread or the plastic part.

The invention further proposes that the plastic part is constructed so as to taper conically towards its tip. It is particularly preferred for the screw thread to project into the plastic part at least in a partial area. As a result the inventive member can easily be screwed in, because its threads can pass in largely unimpeded manner into the threads of the complimentary internal screw thread. A frictional contact only occurs when the tip of the plastic part strikes a corresponding inner end of the internal screw thread and the sides of the plastic part are consequently pressed outwards.

Alternatively thereto (but optionally also in addition thereto) according to a further embodiment of the invention, at least the end portion of the screw threads has lateral recesses which run or extend in the longitudinal direction and engage with complimentary tongues of the plastic part. This embodiment is particularly preferred if the plastic part does not (or not only) cover part of the screw thread and instead fills corresponding recesses in the screw thread, so as in this way to ensure a direct contact between the plastic part and the complimentary internal screw thread for ensuring the desired frictional contact.

The inventive member is used with particular preference in dental prosthetics as an implant extension, implant post, post for attachments, screw for fixing crown, bridges, other structures, etc.

Further features and advantages of the invention can be gathered from the following description of non-limitative embodiments and the attached drawings.

BRIEF DESCRIPTION OF THE DRAWINGS

FIG. 1 is a side view of an embodiment of a screw for fixing crowns, bridges and other structures with a plastic part according to the present invention;

FIG. 2 is a side view of the structure of FIG. 1 rotated by 90° and with portions broken away for purposes of illustration;

FIG. 3 is a top plan view of the screw tip of FIG. 1 without the plastic part;

DESCRIPTION OF THE PREFERRED EMBODIMENTS

Figure 4:
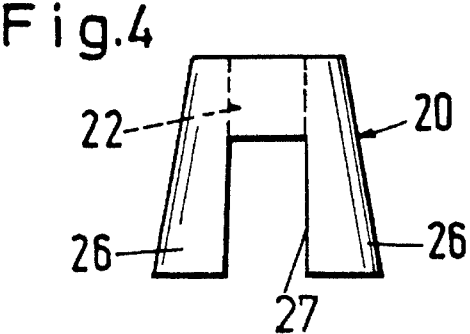
FIG. 4 is a side view of the plastic part for the inventive rotation prevention means.

FIGS. 1 and 2 show in an exemplified manner for the invention a metal screw 1 provided with the inventive rotation prevention means which is a plastic part 20 with two tongues 26 separated by a slot or groove 27, for fixing crowns bridges and other structures. The upper part of the screw 1 with the screw thread 10 is used for screwing into the internal thread of an extension part or into another internal thread. A part or screw head 17 of the screw shown at the bottom of the drawing is used for holding the dental prosthesis. Such a screw 1 can be connected to an implanted member either directly or indirectly, via an intermediate part to be screwed into the member or a corresponding extension.

FIG. 2 shows that the plastic part 20 is constructed so as to conically taper to a point or tip. A tip 12 of the screw is provided with an attachment or projection 14, which engages with a corresponding recess or aperture 22 in the plastic part 20. In the represented care of FIG. 3, both the attachment 14 and the recess 22 in the plastic part 20 are cylindrical and positioned centrally with respect to the cross-section of the screw thread 10 or the plastic part 20. As can also be seen in FIG. 3, in the end portion 13 of the screw thread only two relatively narrow areas of said thread are left, whereas the two larger areas 16 are filled by lateral tongues 26 of skirt means of the plastic part 20. As a result of the conical construction of the plastic part 20 the screw thread 10, as shown in FIG. 2, projects at least partly into the plastic part 20, which leads to the aforementioned advantages on screwing in the member according to the invention.

Figure 5:
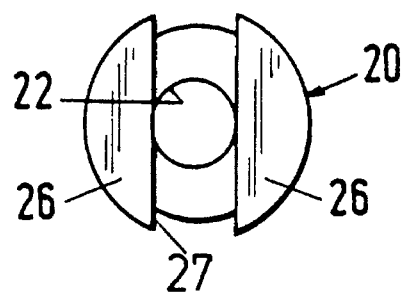
FIG. 5 is a bottom plan view of the plastic part of FIG. 4 taken from the screw side.

The more precise construction with respect to an exemplified embodiment of the plastic part 20 can be gathered from FIGS. 4 and 5. It is readily possible to see the tongues 26 replacing a portion of the screw thread 10 in the end portion 13, the cylindrical recess or hole 22 for engaging with the attachment 14 of the screw 1 and the conical taper of the plastic part 20 towards the tip.

Figure 6:
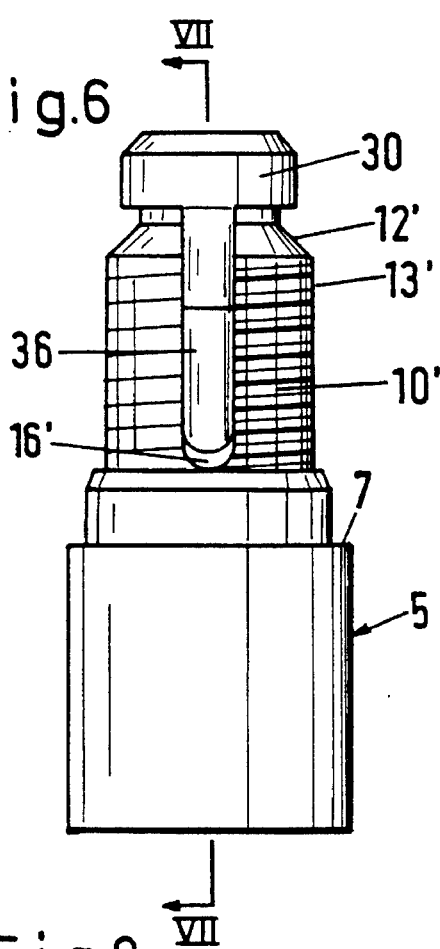
FIG. 6 is a side view of an embodiment of an implant extension provided with an inventive rotation prevention means for use in an enossal tooth implant.
Figure 7:
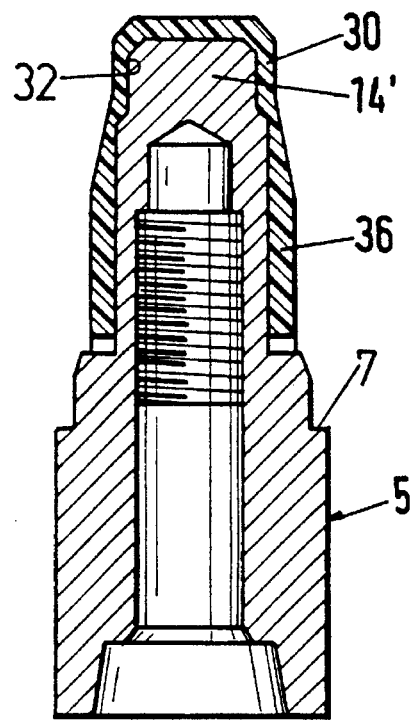
FIG. 7 is a cross sectional view taken on line VII—VII of FIG. 6.

As can be gathered from FIGS. 6 and 7, the inventively sought frictional contact in the vicinity of the screw thread (not shown in FIG. 7) can also be achieved in different ways. The drawing shows in exemplified manner a metal extension or part 5 which can be applied by a shoulder 7 to the upper edge of an implantable member and which can be screwed into the latter and which is also intended for use with an enossal tooth implant, such as can e.g. be used as an intermediate element for a corresponding screw 1. Once again on the tip 12' of the screw thread 10' there is an attachment 14', on which is engaged a corresponding plastic part 30. In the represented embodiment the extension or part 5 also has lateral recesses 16' which run in the longitudinal direction of the screw thread 10' and which engage with complimentary tongues 36 of the plastic part 30. Thus, once again, part of the screw thread 10' is replaced by plastic material.

The tongues 36 of the plastic part 30 are narrower in this case, but longer than in the embodiment of FIGS. 1 and 2. On screwing in the squeezing of the plastic material once again leads to the desired frictional contact. This is achieved either because pressure on the distal end of the plastic part 30 on screwing in the part 5 causes a bulging of the tongues 36, or because the tongues project slightly over the ridges of the screw thread 10' and thereby brings about the corresponding frictional contact.

Figure 8:
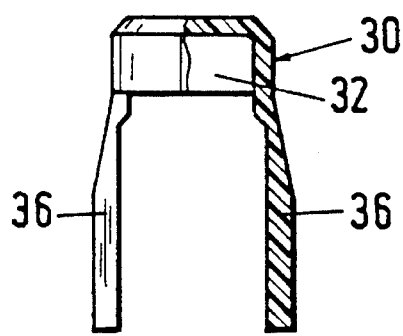
FIG. 8 is a side view with portions broken away of the plastic part for rotation prevention shown in FIGS. 6 and 7.
Figure 9:
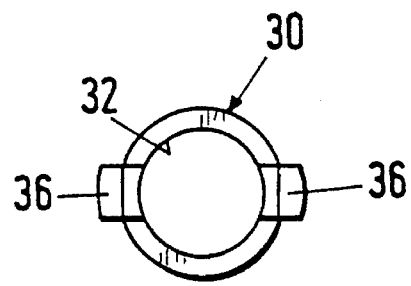
FIG. 9 is a bottom plan view of the plastic part of FIG. 8 taken from the extension part.

FIGS. 8 and 9 show in a similar manner to FIGS. 4 and 5 details of the plastic part 30 of FIGS. 6 and 7 in a part sectional side view or plan view. The lateral tongues 36 and the centrally positioned recess 32 for engagement with the attachment 14' of the extension 5 can easily be seen.

It is obviously also possible (although not shown in the drawings) in the simplest construction of the invention to invert a plastic part with lateral lamellas in one or more portions over the existing screw thread, which does not have recesses, in order to achieve the desired effect. However, the previously described solutions are more durable, due to the reduced wear to the plastic part.

The features of the invention disclosed in the description, drawings and claims can be essential to the realization of the different embodiments of the invention, either singly or in random combination.

We claim:

1. A member comprising external screw threads, a recess extending in a longitudinal direction into an end portion of the threads to interrupt the threads, an end of the member being an attachment projection extending beyond the threads, and means for increasing frictional engagement of the threads when threaded into internal threads of a second member, said means including a plastic part having a socket for receiving said projection and skirt means received in the recess for at least partially replacing the external screw threads of the member.

2. A member according to claim 1 wherein both the socket and the projection are cylindrical, said projection is positioned centrally with respect to the cross section of the member and said socket is centrally position with respect to the cross section of the plastic part.

3. A member according to claim 2, wherein the plastic part tapers conically toward a tip of the part.

4. A member according to claim 3, wherein said skirt means has a recess forming a partial area and at least a portion of the screw threads project into said partial area of the skirt means.

5. A member according to claim 3, wherein the member has more than one recess extending into the screw threads and the skirt means has a complementary tongue received in each recess in the screw threads.

6. A member according to claim 1, wherein the member has more than one recess extending into the screw threads adjacent to the projection, said skirt means includes a tongue extending into each of the recesses.

7. A member according to claim 6, wherein said tongues are separated by a transverse slot in the plastic part and said socket is an aperture in the base of the plastic part.

8. A member according to claim 6, wherein each of said tongues has a length substantially greater than the width of the tongue and each of the recesses extends substantially a full length of the external screw threads on said member.

9. A member comprising external screw threads, a tip with an attachment projection extending beyond the threads, a recess extending longitudinally into the screw threads to interrupt the threads, and means for increasing frictional engagement of the threads when threaded into internal threads of a second member, said means including a plastic part having a socket for receiving said projection and skirt means for extending into the recess.

10. A member according to claim 9, wherein the socket is cylindrical and is located centrally in the plastic part and the projection is a cylindrical projection on an axis of the member.

11. A member according to claim 10, wherein the plastic part tapers conically toward a tip of the part.

12. A member according to claim 11, wherein the skirt means has at least one recess forming a partial area for receiving a portion of the external screw threads of the member.

13. A member according to claim 11, wherein the screw threads are provided with more than one recess extending in a longitudinal direction, and said skirt means includes complementary tongues of the plastic part received in said recesses.

14. A member according to claim 9, wherein the member has more than one recess extending in the external screw threads adjacent to the projection, said skirt means of the plastic part including tongues received in said recesses.

15. A member according to claim 14, wherein said tongues are separated by a transverse slot in the plastic part and said socket is an aperture in the base of the plastic part.

16. A member according to claim 14, wherein each of said tongues has a length substantially greater than the width of the tongue and each of the recesses extends substantially a full length of the external screw threads on said member.

* * * * *